United States Patent
Eden

(10) Patent No.: US 9,101,738 B2
(45) Date of Patent: Aug. 11, 2015

(54) GUIDE WIRE HOLDER ADAPTED FOR FIXATION TO A MEDICAL DEVICE

(75) Inventor: Ingo Eden, Rohrdorf-Achenmuehle (DE)

(73) Assignee: Medi-Globe GmbH, Rohrdorf-Achenmuehle (DE)

( * ) Notice: Subject to any disclaimer, the term of this patent is extended or adjusted under 35 U.S.C. 154(b) by 88 days.

(21) Appl. No.: 13/580,462

(22) PCT Filed: Feb. 28, 2011

(86) PCT No.: PCT/DE2011/000180
§ 371 (c)(1),
(2), (4) Date: Aug. 22, 2012

(87) PCT Pub. No.: WO2011/110152
PCT Pub. Date: Sep. 15, 2011

(65) Prior Publication Data
US 2012/0323146 A1    Dec. 20, 2012

(30) Foreign Application Priority Data
Mar. 12, 2010   (DE) .......................... 10 2010 011 222

(51) Int. Cl.
*A61M 25/09* (2006.01)
*A61B 1/00* (2006.01)
*A61B 1/012* (2006.01)

(52) U.S. Cl.
CPC ........ *A61M 25/09041* (2013.01); *A61B 1/0014* (2013.01); *A61B 1/012* (2013.01); *A61M 2025/09125* (2013.01)

(58) Field of Classification Search
CPC ................ A61B 1/0014; A61B 1/012; A61M 25/09041; A61M 2025/09125
USPC .......................................................... 600/585
See application file for complete search history.

(56) References Cited

U.S. PATENT DOCUMENTS 4,844,092 A    7/1989    Rydell et al.
6,096,009 A    8/2000    Windheuser et al.
(Continued)

FOREIGN PATENT DOCUMENTS

DE    699 26 124    12/2005
EP    1 079 883    3/2001
(Continued)

OTHER PUBLICATIONS

International Search Report of PCT/DE2011/000180, Jul. 26, 2011.

*Primary Examiner* — Lee S Cohen
*Assistant Examiner* — Emily Lloyd
(74) *Attorney, Agent, or Firm* — Collard & Roe, P.C.

(57) ABSTRACT

A guide wire holder for receiving and securing a medical guide wire and for mounting on a medical appliance has a mounting part through which the guide wire can be guided, and a guide wire support which is connected to and protrudes from the mounting part and allows the guide wire to be secured by a guide wire receiver. The guide wire receiver contains a guide wire deflector that tensions and deflects the guide wire in a direction leading away from its direction of passage through the mounting part. The guide wire receiver is followed by an additional guide wire deflector that is formed with a guide wire contact surface, on which the guide wire can be guided along a guide track, so that a frictional resistance can be exerted relative to the guide wire guided over the top of the guide wire support.

8 Claims, 2 Drawing Sheets

(56) References Cited

U.S. PATENT DOCUMENTS

| | | |
|---|---|---|
| 6,663,597 B1 | 12/2003 | Windheuser et al. |
| 7,060,052 B2 | 6/2006 | Windheuser et al. |
| 7,637,863 B2 | 12/2009 | Deal et al. |
| 7,670,316 B2 | 3/2010 | Windheuser et al. |
| 8,206,283 B2 | 6/2012 | Windheuser et al. |
| 2004/0162465 A1 | 8/2004 | Carrillo |
| 2006/0195117 A1 | 8/2006 | Rucker et al. |

FOREIGN PATENT DOCUMENTS

| | | |
|---|---|---|
| EP | 1 654 026 | 5/2006 |
| WO | WO 2007/086876 | 8/2007 |

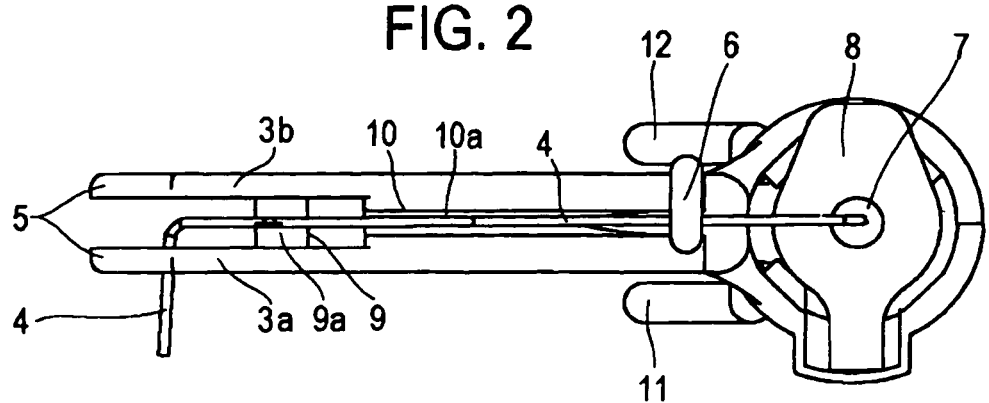
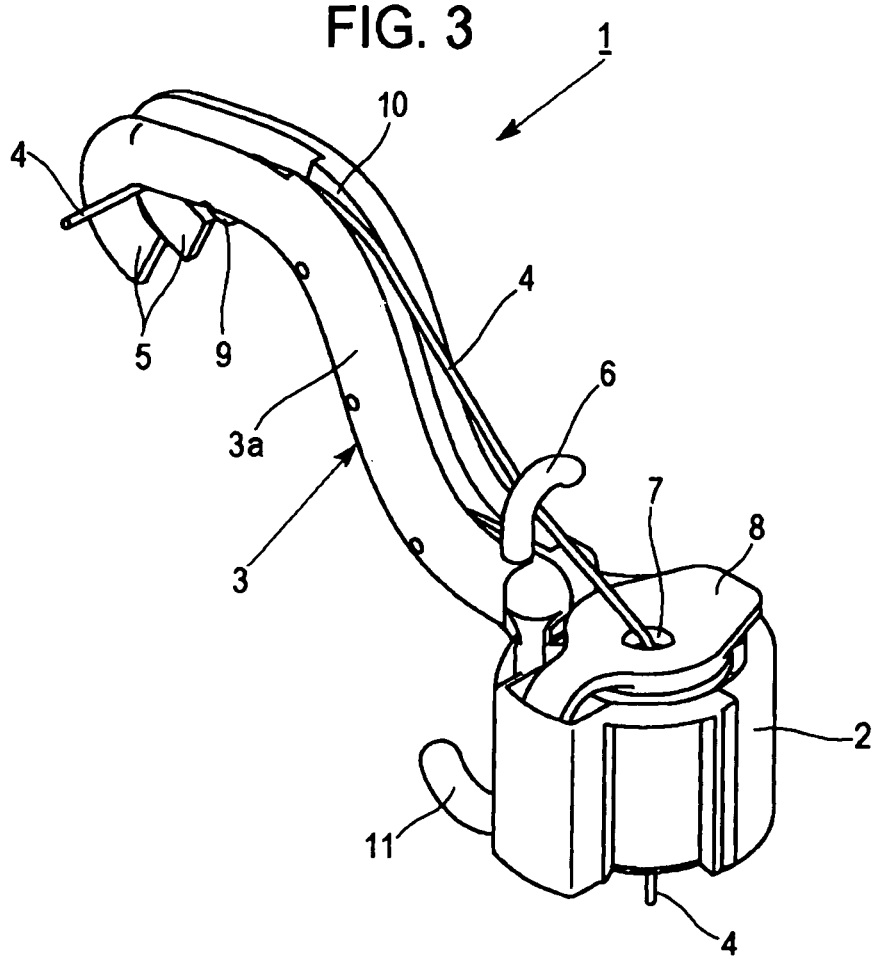

GUIDE WIRE HOLDER ADAPTED FOR FIXATION TO A MEDICAL DEVICE

CROSS REFERENCE TO RELATED APPLICATIONS

This application is the National Stage of PCT/DE2011/000180 filed on Feb. 28, 2011, which claims priority under 35 U.S.C. §119 of German Application No. 10 2010 011 222.4 filed on Mar. 12, 2010, the disclosure of which is incorporated by reference. The international application under PCT article 21(2) was not published in English.

BACKGROUND OF THE INVENTION

The invention relates to a guide wire holder for accommodating a medical guide wire and holding it in place, and for being affixed to a medical device, particularly to an endoscope. The guide wire holder has an affixation part through which the guide wire can be passed, and a guide wire carrier that is connected with the affixation part and projects away from the affixation part. The carrier permits holding the guide wire in place by means of a guide wire accommodation device, which contains a guide wire deflection element that deflects and tenses the guide wire at a distance from the affixation part, in a direction that leads away from a pass-through direction in the affixation part. The element is followed, at a further distance from the affixation part, by an additional guide wire deflection element.

According to the previously known state of the art, there are two fundamentally different solutions for holding a guide wire in place. According to the one solution, the friction at a plurality of projections having deflection surfaces that might have edges is utilized; these projections project laterally from a carrier part connected with an affixation part, and the guide wire is threaded around them. According to the other solution, the friction at the edges of openings that are situated in a holder plate is utilized; this plate can be affixed to a medical device by means of an affixation part.

A guide wire holder that serves for attachment of an elongated medical device, namely a guide wire on an elongated introduction device, particularly on an endoscope, belongs to the first solution mentioned (U.S. Pat. No. 7,637,863 B2; EP 1 654 026 B1). In this connection, the guide wire holder has a rib part that extends away from an affixation part for its affixation on an endoscope, on which part at least three projections that extend outward are provided, around which the guide wire is threaded. In this connection, the multiple projections make contact, in terms of friction, on opposite sides of the guide wire, at a distance from one another. Although relatively secure holding in place of a guide wire on the guide wire holder is made possible in this way, there is nevertheless a wish for a simpler holder structure, as compared with this known guide wire holder.

Furthermore, a guide wire holder (WO 2007/086876 A2) that has a guide wire deflection part and a guide wire securing part, which is provided with projections and/or grooves, belongs to the solution first mentioned. These projections and/or grooves are provided, as in the case of the known guide wire holder considered above, at least in triplicate. Although relatively secure holding in place of a guide wire on the guide wire holder is made possible in this way, too, the wish for a simpler holder structure as compared with this known guide wire holder nevertheless exists in this case, too.

A guide wire and catheter locking device (U.S. Pat. No. 7,060,052 B2; EP 1 079 883 B1; DE 699 26 124 T2) that can be affixed to an endoscope with an affixation device and that has an introduction opening for introduction of a guide wire in an essentially rigid body part that extends from the affixation device, and a locking slit for clamping the guide wire formed in the introduction opening, belongs to the other solution mentioned above. However, this method of securing the guide wire, with regard to its displacement, is sometimes not sufficient. Furthermore, the outside of the guide wire can be damaged as the result of even a slight displacement in the clamping position, as the result of excessively strong friction at the edges of the locking slit. Such a damaged guide wire is then no longer suitable for further use and therefore cannot be used.

SUMMARY OF THE INVENTION

The invention is therefore based on the task of developing a guide wire holder of the type indicated initially further, so that a simpler holder structure than in the case of the two known guide wire holders considered initially and, at the same time, also secure accommodation of a guide wire are ensured.

The task indicated above is accomplished, in the case of a guide wire holder of the type indicated initially, according to the invention, in that the additional guide wire deflection element is formed by a guide wire contact surface on the guide wire carrier, on which surface the guide wire can be guided along a guide track, by means of which a friction resistance can be exerted in the region of the guide wire contact surface, so that the guide wire is guided over the top of the guide wire carrier.

The invention therefore uses a different principle for exerting a friction effect on the guide wire, in order to hold a guide wire in place in a guide wire carrier, than the two known holding in place principles considered above. According to the invention, a friction effect on the guide wire can be exerted by means of the guide track provided for accommodation of the guide wire on the guide wire carrier.

The invention brings with it the advantage that not only a simpler holder structure but also more secure accommodation of the guide wire are achieved than in the case of the two known guide wire holders considered initially.

Preferably, the guide track between the guide wire deflection element and the guide wire contact surface contains a further guide wire contact surface on the top of the guide wire carrier, and a further friction resistance with regard to the guide wire guided over the top of the guide wire carrier can be exerted by means of this further guide wire contact surface. This measure brings with it the advantage that the friction resistance that can be exerted on the guide wire on or the guide wire carrier can be further increased.

It is practical if the guide track of the guide wire is formed by means of a carrier region that lies below the top of the guide wire carrier, in which region the guide wire can be accommodated by both guide wire contact surfaces. In this way, the advantage of particularly secure guidance of the guide wire on the top of the guide wire carrier is obtained.

According to a further practical embodiment of the invention, the further guide wire contact surface is roughened. This results in the advantage of a reinforced friction resistance with regard to the guide wire guided over the top of the guide wire carrier.

According to yet another practical embodiment of the invention, the one guide wire contact surface is formed by a roller device contained in the guide wire carrier. This roller device, which can be used, in advantageous manner, for reversing the direction of the guide track of the guide wire, is preferably a roller device that is fixed in place.

According to another practical further development of the invention, the roller device is formed by two roller device parts that are brought together in a resilient manner, between which the guide wire can be accommodated. In this way, a relatively strong friction force can be exerted on the guide wire by way of the roller device, which force can be adapted to different requirements with regard to the clamping force to be exerted on the guide wire, by means of corresponding establishment of the spring force that brings the roller device parts together.

It is practical if the roller devices mentioned above are formed by a single roller element. This brings with it the advantage of a particularly simple roller construction.

According to yet another practical embodiment of the invention, the guide wire carrier contains two carrier arms connected with one another, having the two guide wire contact surfaces preferably disposed between these carrier arms. This brings with it the advantage that the guide track for the guide wire can be formed in a particularly simple manner, on the top of the guide wire carrier.

It is practical if the guide wire carrier has an S-shaped progression when looked at from one side. In this way, the guide track for the guide wire can achieve an excellent clamping effect on the guide wire.

Preferably, the guide wire carrier has an offset region on its end that lies at a distance from a connection location on the affixation part, in which region the guide wire can be deflected at an angle out of its guide track on the top of the guide wire carrier. In this manner, it is possible to additionally clamp the guide wire, in advantageous manner, in its end that lies at a distance from a connection location on the affixation part, taking advantage of the offset region, and furthermore to conduct it in a desired direction from the guide wire carrier, and thereby away from the guide wire holder.

BRIEF DESCRIPTION OF THE DRAWINGS

The invention will be explained in greater detail below, using an exemplary embodiment and using drawings.

In the drawings, the figures show.

Before the drawings are discussed in further detail, it should be noted that in all the drawings, devices or elements that are the same or correspond to one another are referred to with the same reference symbols.

DETAILED DESCRIPTION OF THE PREFERRED EMBODIMENTS

Figure 1A:
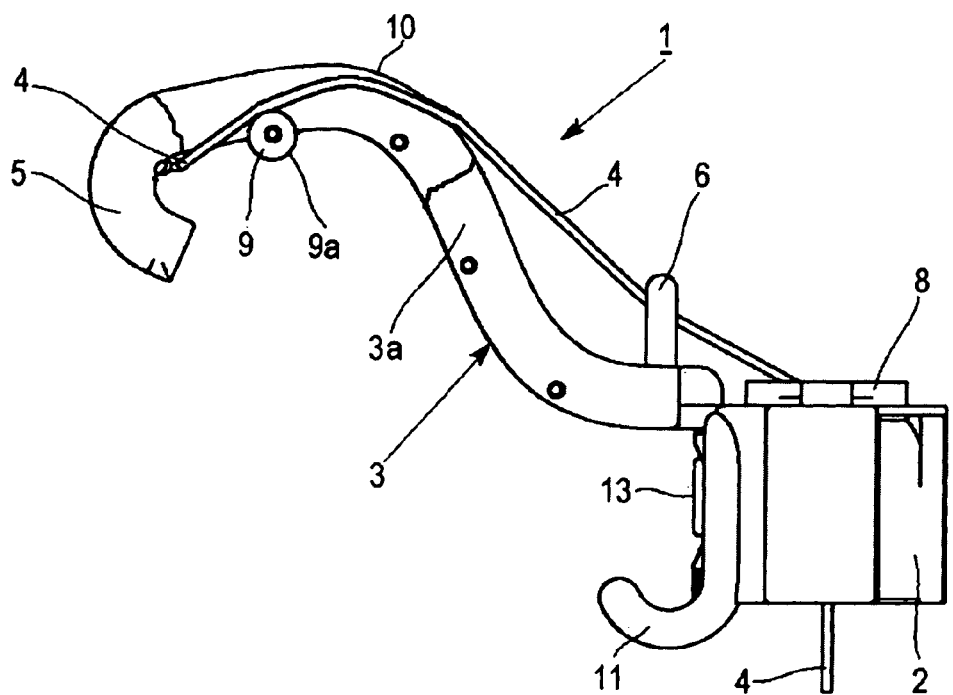
FIG. 1a a schematic side view of a guide wire holder according to an embodiment of the invention, in a size that can be different from the size used in practice, FIG. 1b a schematic opposite side view of the guide wire holder according to FIG. 1a, in which the guide wire carrier has been cut away to show the interior, FIG. 2 a top view of the guide wire holder shown in FIGS. 1a and 1b, according to an embodiment of the invention, and FIG. 3 a perspective view of the guide wire holder shown in FIGS. 1a, 1b and 2, according to an embodiment of the invention.
Figure 1B:
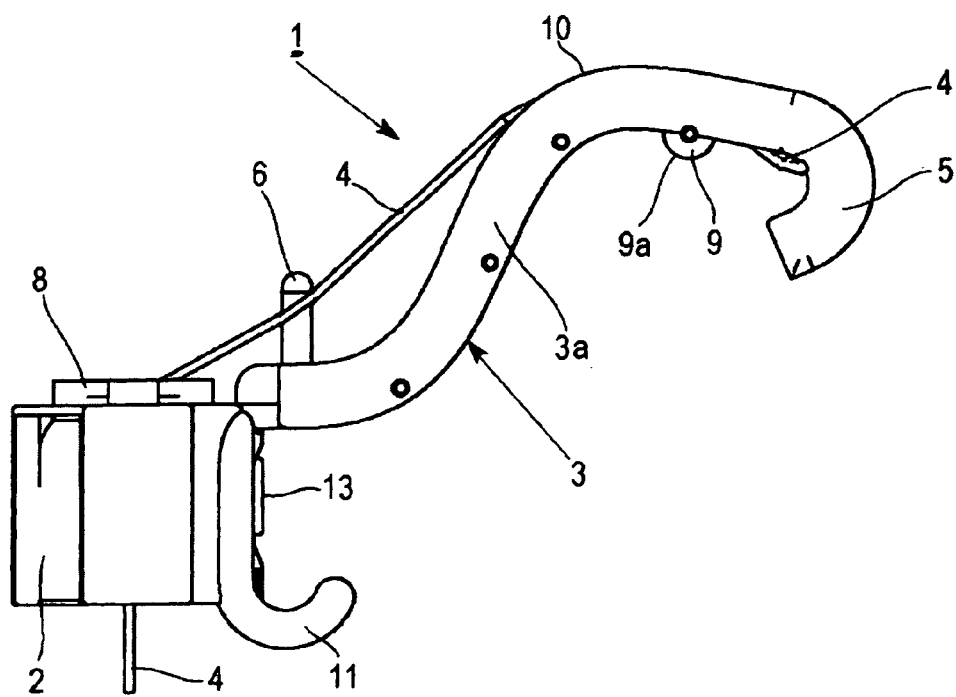

In FIGS. 1a and 1b, a guide wire holder 1 according to an embodiment of the invention is shown. This guide wire holder 1 contains an affixation part 2 for affixing the guide wire holder 1 on a medical device (not shown here), which can particularly be an endoscope, on the working channel connection of which the affixation part 2 in question can be affixed. In place of an endoscope, however, a different medical guide wire introduction device is a possibility, if applicable. The affixation part 2 can be, for example, a set-on part or a cap that can be set onto an accommodation part of the medical device, in each instance, and can easily be pulled off from there. However, the affixation part 2 in question can also contain a screw connection part, if applicable, with which it can be screwed onto or into a corresponding screw connection part of the medical device, in each instance.

A guide wire carrier 3 is connected with the affixation part 2, which carrier permits holding a guide wire 4 in place by means of a guide wire accommodation device. The guide wire carrier 3, as is clearly evident from FIGS. 2 and 3, contains two carrier arms 3a and 3b connected with one another. The connection of the two carrier arms 3a and 3b is indicated by means of small circles on the carrier arm 3a in FIGS. 1a, 1b and 3. The two carrier arms 3a and 3b can, however, preferably be elements of a single molded part, to which yet other elements of the guide wire holder 1 can belong, if applicable, as will still become evident in greater detail below. In FIG. 1a, carrier arm 3b is cut away to show the interior of the device.

The guide wire carrier 3 and therefore its two carrier arms 3a and 3b have an S-shaped progression as shown in FIGS. 1a and 1b. In accordance with this S-shaped progression, the two carrier arms 3a and 3b rise upward from the affixation part 2, drop down after having reached a specific, established height, and finally end in an offset region 5. In this offset region 5, the region between the two carrier arms 3a and 3b is open, starting from a guide wire deflection element 9 that will still be considered in greater detail below.

The guide wire accommodation device of the guide wire carrier 3 permits holding the guide wire 4 in place so that this wire cannot be displaced or pulled in its longitudinal direction. For this purpose, the guide wire accommodation device comprises a guide wire deflection element 6 that rises on a flat initial region of the guide wire carrier 3 and is configured as a deflection bracket or retainer that is open on one side. This guide wire deflection element 6 deflects the guide wire 4, at a distance from the affixation part 2, in a direction that leads away from its pass-through direction in the affixation part 2, and in this connection tenses the guide wire 4, as is evident from FIG. 1. The guide wire 4 is thereby deflected out of its pass-through direction in the affixation part 2 so as to lie against an upper edge of a pass-through opening 7 of a cover plate 8 of the affixation part 2. A friction effect is therefore exerted on the guide wire 4 at this contact location.

The guide wire accommodation device comprises an additional guide wire deflection element 9 that has already been mentioned, at a further distance from the affixation part 2. Guide wire deflection element 9 is formed by a guide wire contact surface on the top of the guide wire carrier 3; i.e., between the two carrier arms 3a and 3b of the guide wire carrier 3, which are connected with one another by means of this guide wire deflection element 9. The guide wire 4 can be guided along a guide track on the contact surface of guide wire deflection element 9, by means of which track a friction resistance with regard to the guide wire 4 that is guided over the top of the guide wire carrier 3 can be exerted, in the region of the guide wire contact surface. The guide track preferably runs, as is evident from FIGS. 1 to 3, on the top of the guide wire carrier 3 and between its carrier arms 3a and 3b, specifically approximately in the middle between these carrier arms 3a and 3b.

The additional guide wire deflection element 9 is formed, in the case of the present embodiment, by means of a roller device provided with the same reference symbol 9, contained in the guide wire carrier 3, which device is formed here by a single roller element 9. This roller element 9 can be a fixed roller element or a roller element that can be turned only with difficulty when the guide wire 4 is pulled over this roller element. In both cases, the roller element 9 can possess a rough surface, so that the guide wire 4 pulled over this roller element 9 is countered with a friction resistance.

Alternatively, the roller device 9 can be formed by two roller device parts that are brought together in a resilient manner, between which the guide wire 4 can be accommodated. In this case, too, the two roller device parts can each have a rough surface, so that the guide wire 4 pulled over the roller element parts is countered with a friction resistance.

In addition to the guide track explained between the guide wire deflection element 6 and the additional guide wire deflection element 9 with its contact surface 9a, a further guide wire deflection element 10 with a contact surface 10a is provided here, on the top of the carrier arms 3a and 3b of the guide wire carrier 3, which are connected with one another here, as is evident in greater detail from FIGS. 2 and 3. A further friction resistance with regard to the guide wire 4 that is guided over the top of the guide wire carrier 3 can be exerted by means of this further guide wire contact surface 10a, which is situated on the uppermost arc-shaped upper section of the guide wire carrier 3 and which is preferably also roughened. The arc-shaped upper section 10a of the guide wire carrier 3 represents an elevation of a connection line that runs directly between the guide wire deflection element 6 and the guide wire contact surface 9a.

The roughness of the aforementioned guide wire contact surfaces 9a and 10a can be achieved, for example, by means of structuring of these surfaces and/or by means of a correspondingly rough surface coating applied to the surfaces in question.

The aforementioned guide track of the guide wire 4 is formed here by a carrier region that lies below the top of the guide wire carrier 3, in which region the guide wire 4 can be accommodated by guide wire contact surface 9a and guide wire contact surface 10a. The distance of the guide track from the top of the guide wire carrier 3 lies between, for example, 0.5 mm and 4 mm.

In addition to the elements described above, the guide wire holder 1 shown in FIGS. 1 to 3 also has two hooks 11, 12 that are affixed, together with the guide wire carrier 3, on the affixation part 2, below an opening 13 of the affixation part 2, which opening is connected with a passage of the affixation part 2 for the guide wire 4. A collection bag (not shown) can be suspended on the two hooks 11, 12. The collection bag can collect liquid that might exit from the opening 13 when the guide wire 4 is pulled out.

For working with the guide wire 4 in connection with a medical device (not shown) such as an endoscope, the guide wire 4 is first introduced through the opening 7 of the cover plate 8 of the affixation part 2 set onto the medical device, to such an extent until the tip (not shown) of the guide wire 4 has been advanced into a desired target region. Then, the section of the guide wire 4 that projects out of the opening 7 of the cover plate 8 of the affixation part 2, after having been guided down under the guide wire deflection element 6, is laid into the guide track on or close to the top of the guide wire carrier 3, in order to come into contact with the guide wire contact surface 9a and the further guide wire contact surface 10a. Subsequently, the part of the guide wire 4 that lies away from these contact surfaces 9a and 10a and therefore farthest away from the opening 7 of the cover plate 8 of the affixation part 2 is laid around one of the carrier arms 3a and 3b of the guide wire carrier 3—here around the carrier arm 3a. As a result, the guide wire 4 is deflected at an angle, specifically by about 90° out of its guide track on or close to the top of the guide wire carrier 3, as is evident from FIG. 2. The guide wire 4 has thereby been tightened in a desired direction, so that it can now no longer be displaced in its longitudinal direction on the guide wire carrier 3.

For this non-displaceability of the guide wire 4 in its longitudinal direction on the guide wire carrier 3, the guide wire 4 must have contact at the exit location from the cover plate 8 of the affixation part 2, at the guide wire deflection element 6 on or at the top of the guide wire carrier 3, and at the guide wire contact surface 9a on or close to the top of the guide wire carrier 3. The contacts of the guide wire 4 at the further guide wire contact surface 10a and on the offset region 5 of the guide wire carrier 3 have a supporting effect on the non-displaceability of the guide wire 4 in its longitudinal direction on the guide wire carrier 3, as explained above.

In conclusion, the affixation part 2 can consist of a biocompatible material, such as a metal or plastic, for example of a rubber material. All the other elements of the guide wire holder 1 described here also consist of a biocompatible material, such as a metal or plastic, such as, for example, of an ABS plastic (acrylonitrile/butadiene/styrene copolymerizate), specifically preferably as a single, cohesive molded or injection-molded part. In this connection, edges of parts of the guide wire holder 1 along which the guide wire 4 is guided are preferably rounded, in order to avoid damage of the guide wire surface and to simplify laying of the guide wire 4 into the guide wire holder 1 for the user.

The guide wire 4 consists, as is known, of a stainless steel core that is mantled by means of polytetrafluoroethylene—PTFE—(trade name: TEFLON®).

REFERENCE SYMBOL LIST

1 guide wire holder
2 affixation part
3 guide wire carrier
3a carrier arm
3b carrier arm
4 guide wire
5 offset region
6 deflection element
7 passage opening
8 cover plate
9 guide wire deflection element, roller device, roller
9a guide wire contact surface
10 guide wire deflection element
10a guide wire contact surface
11 hook
12 hook
13 opening

The invention claimed is:

1. A guide wire holder for accommodating a medical guide wire and holding the guide wire in place, the guide wire holder being adapted to be affixed to a medical device, the guide wire holder comprising:
    an affixation part configured to allow passage of the guide wire therethrough;
    a guide wire carrier connected with the affixation part and projecting away from the affixation part, said carrier having a guide wire accommodation device comprising:
        a first guide wire deflection element disposed at a distance from the affixation part, the first guide wire deflection element being configured for deflecting and tensing the guide wire in a direction away from a longitudinal direction of the guide wire in the affixation part, and a second guide wire deflection element disposed at a further distance from the affixation part than the first guide wire deflection element, wherein the first guide wire deflection element is formed by a deflection bracket or retainer that extends upward from an initial region of the guide wire carrier and is open on one side, wherein the guide wire carrier contains two carrier arms connected with one another by the second guide wire deflection element, wherein the second guide wire deflection element is formed by a guide wire contact surface on a top of the guide wire carrier between the two carrier arms of the guide wire carrier, said guide wire contact surface forming a guide track for the guide wire and said guide wire contact surface being configured for exerting a friction resistance on the guide wire, wherein the two carrier arms each have an offset part located on an end of the carrier arms that lies furthest from the affixation part, wherein a space between the offset parts of the carrier arms is open, and wherein the offset part of each carrier arm is configured so that the guide wire can be laid around one of the offset parts to deflect the guide wire at an angle of about 90 degrees out of the guide track and away from the guide wire holder.

2. The guide wire holder according to claim 1, wherein the guide wire contact surface forms a first guide wire contact surface, and further comprising a further guide wire deflection element having a second guide wire contact surface, the second guide wire contact surface being disposed between the first guide wire deflection element and the first guide wire contact surface, and wherein said second guide wire contact surface is configured to exert a friction resistance on the guide wire.

3. The guide wire holder according to claim 2, wherein the first guide wire contact surface and the second guide wire contact surface form a carrier region for the guide wire below the top of the guide wire carrier.

4. The guide wire holder according to claim 2, wherein the second guide wire contact surface is rough.

5. The guide wire holder according to claim 2, wherein the first guide wire contact surface is formed by a roller device contained in the guide wire carrier.

6. The guide wire holder according to claim 5, wherein the roller device is formed by two roller device parts that are resiliently connected to each other, and wherein the roller device is configured for accommodating the guide wire between said roller device parts.

7. The guide wire holder according to claim 5, wherein the roller device is formed by a single roller element.

8. The guide wire holder according to claim 1, wherein the guide wire carrier forms a shape with two curves in opposite directions.

* * * * *